US00PP37825P2

(12) United States Plant Patent
Hofmann

(10) Patent No.: US PP37,825 P2
(45) Date of Patent: Oct. 27, 2026

(54) ***MANDEVILLA* PLANT NAMED 'INMAN 501'**

(50) Latin Name: *Mandevilla sanderi*
Varietal Denomination: INMAN 501

(71) Applicant: INNOVAPLANT ZIERPFLANZEN GmbH & Co. KG, Gensingen (DE)

(72) Inventor: Birgit Hofmann, Rudesheim am Rhein (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 19/546,385

(22) Filed: Feb. 22, 2026

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
CPC . A01H 5/02; A01H 5/00; A01H 6/088; A01H 6/08
See application file for complete search history.

(56) References Cited

U.S. PATENT DOCUMENTS

PP24,124 P2 * 12/2013 Lannes ..... A01H 5/02 Plt./232

* cited by examiner

*Primary Examiner* — June Hwu
(74) *Attorney, Agent, or Firm* — C. Anne Whealy

(57) ABSTRACT

A new and distinct cultivar of *Mandevilla* plant named 'INMAN 501', characterized by its broadly upright plant habit; moderately vigorous growth habit and moderate growth rate; freely branching habit; dense and bushy appearance; dark green-colored leaves; early, freely and continuous flowering habit; and medium to large star-shaped deep red-colored flowers with reddish orange-colored throats.

2 Drawing Sheets

Figure 1:
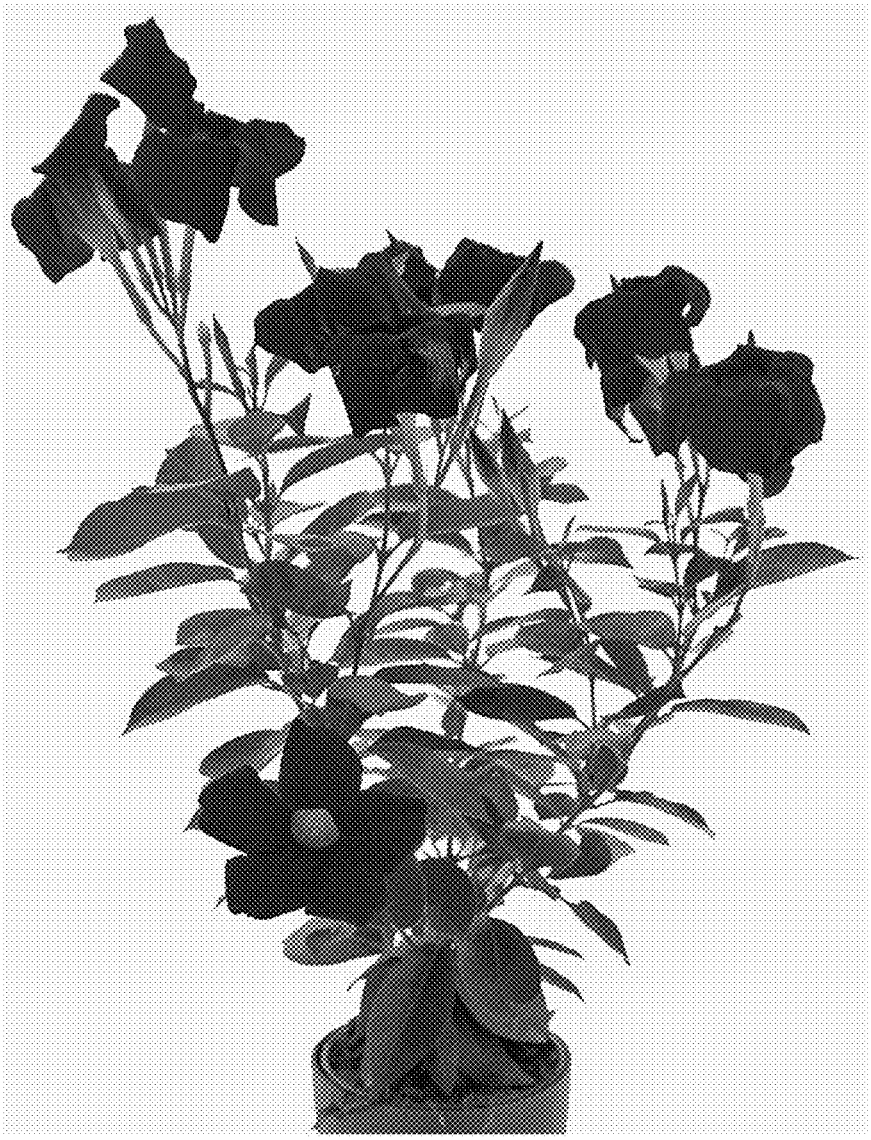

Botanical designation: *Mandevilla sanderi*.
Cultivar denomination: 'INMAN 501'.

CROSS-REFERENCED TO CLOSELY-RELATED APPLICATIONS

A European Community Plant Breeder's Rights application for the instant plant was filed by the Applicant/Assignee of the instant application, Innovaplant Zierpflanzen GmbH & Co. KG of Gensingen, Germany on Aug. 4, 2025, application number 2025/1740, and published on Oct. 15, 2025. Foreign priority is not claimed to this European Community Plant Breeder's Rights application.

BACKGROUND OF THE INVENTION

The present invention relates to a new and distinct cultivar of *Mandevilla* plant, botanically known as *Mandevilla sanderi* and hereinafter referred to by the name 'INMAN 501'.

The new *Mandevilla* plant is a product of a planned breeding program conducted by the Inventor in Johannesburg, South Africa and Heidesheim, Germany. The objective of the breeding program is to create new freely branching *Mandevilla* plants that flower early and freely and have attractive flowers that resist fading and sunscalding.

The new *Mandevilla* plant originated from a cross-pollination conducted by the Inventor in Johannesburg, South Africa in January, 2020 of a proprietary breeding selection of *Mandevilla sanderi* identified as code number d17-4561-8, not patented, as the female, or seed parent with a proprietary breeding selection of *Mandevilla sanderi* identified as code number d17-4014-1, not patented, as the male, or pollen, parent. The new *Mandevilla* plant was discovered and selected by the Inventor as a single flowering plant from within the progeny of the stated cross-pollination in a controlled greenhouse environment in Heidesheim, Germany in June, 2022.

Asexual reproduction of the new *Mandevilla* plant by vegetative cuttings in a controlled greenhouse environment in Heidesheim, Germany since July, 2022 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INMAN 501'. These characteristics in combination distinguish 'INMAN 501' as a new and distinct *Mandevilla* plant:

1. Broadly upright plant habit.
2. Moderately vigorous growth habit and moderate growth rate.
3. Freely branching habit; dense and bushy appearance.
4. Dark green-colored leaves.
5. Early, freely and continuous flowering habit.
6. Medium to large star-shaped deep red-colored flowers with reddish orange-colored throats.

Plants of the new *Mandevilla* can be compared to plants of the female parent selection. Plants of the new *Mandevilla* differ primarily from plants of the female parent selection in the following characteristics:

1. Plants of the new *Mandevilla* are denser and bushier than plants of the female parent selection.
2. Plants of the new *Mandevilla* flower earlier than plants of the female parent selection.
3. Flowers of plants of the new *Mandevilla* are smaller than flowers of plants of the female parent selection.

Plants of the new *Mandevilla* can be compared to plants of the male parent selection. Plants of the new *Mandevilla* differ primarily from plants of the male parent selection in the following characteristics:

1. Plants of the new *Mandevilla* are denser and bushier than plants of the male parent selection.
2. Flowers of plants of the new *Mandevilla* are flatter than and not as revolute as flowers of plants of the male parent selection.
3. Flowers of plants of the new *Mandevilla* are larger than flowers of plants of the male parent selection.

Plants of the new *Mandevilla* can also be compared to plants of *Mandevilla sanderi* 'Lanidaho', disclosed in U.S. Plant Pat. No. 24,124. In side-by-side comparisons, plants of the new *Mandevilla* differ primarily from plants 'Lanidaho' in the following characteristics:

1. Plants of the new *Mandevilla* are denser and bushier than plants of 'Lanidaho'.
2. Plants of the new *Mandevilla* flower earlier than plants of 'Lanidaho'.
3. Plants of the new *Mandevilla* have darker red-colored flowers than plants of 'Lanidaho'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'INMAN 501' grown in a container.

Figure 2:
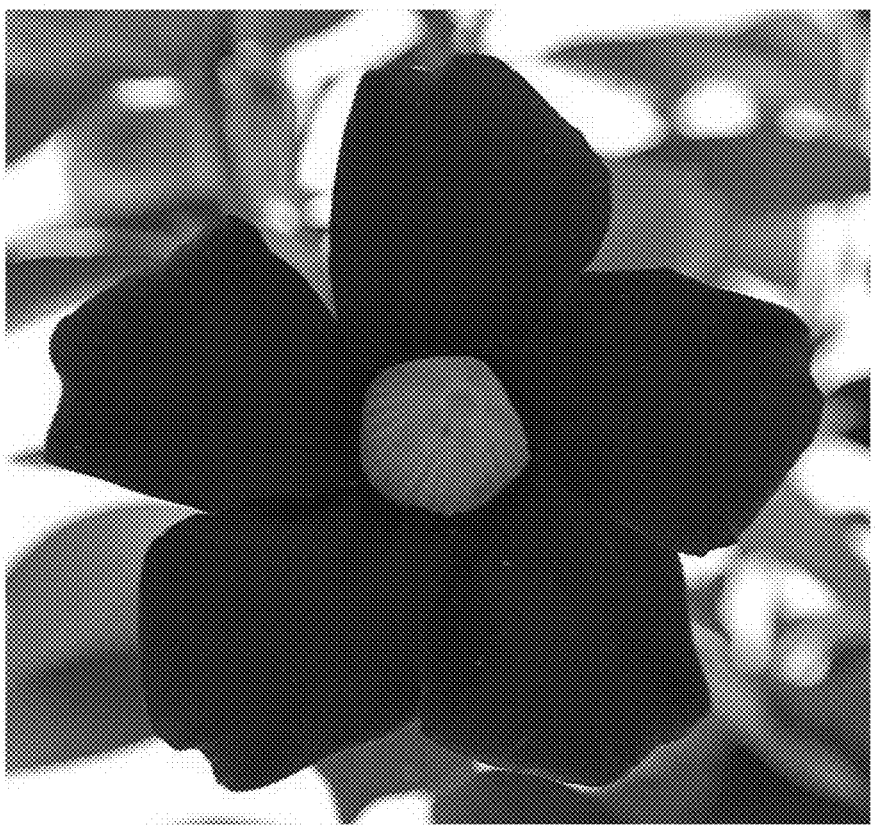

The photograph on the second sheet (FIG. 2) is a close-up view of a typical flower of 'INMAN 501'.

DETAILED BOTANICAL DESCRIPTION

The aforementioned photographs and following observations, measurements and values describe plants grown during the summer in 12-cm containers in a glass-covered greenhouse in Heidesheim, Germany and under cultural practices typical of commercial *Mandevilla* production. During the production of the plants, day temperatures ranged from 12° C. to 35° C. and night temperatures ranged from 12° C. to 18° C. Plants were pinched one time and were four months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'INMAN 501'.

Parentage:

*Female, or seed, parent*.—Proprietary breeding selection of *Mandevilla sanderi* identified as code number d17-4561-8, not patented.

*Male, or pollen, parent*.—Proprietary breeding selection of *Mandevilla sanderi* identified as code number d17-4014-1, not patented.

Propagation:

*Type*.—By vegetative cuttings.

*Time to initiate roots, summer*.—About three weeks at temperatures ranging from 20° C. to 35° C.

*Time to initiate roots, winter*.—About three weeks at temperatures ranging from 20° C. to 25° C.

*Time to produce a rooted young plant, summer*.—About 20 to 25 days at temperatures ranging from 20° C. to 35° C.

*Time to produce a rooted young plant, winter*.—About 25 to 30 days at temperatures ranging from 20° C. to 25° C.

*Root description*.—Thick, fleshy; typically white in color, actual color of the roots is dependent on substrate composition, water quality, fertilizers, substrate temperature and physiological age of roots.

*Rooting habit*.—Low branching; medium density.

Plant description:

*Plant and growth habit*.—Broadly upright plant habit; roughly broadly obovate in overall shape; moderately vigorous growth habit and moderate growth rate; and freely branching habit; dense and bushy appearance.

*Plant height, soil level to top of foliar plane*.—About 39.5 cm.

*Plant height, soil level to top of floral plane*.—About 38 cm.

*Plant diameter (spread)*.—About 33 cm.

*Lateral branch description*.—Branching habit: Freely branching habit, typically about three primary lateral branches per plant each with about two secondary lateral branches; pinching enhances lateral branch development. Length: About 19 cm. Diameter: About 2 mm. Internode length: About 2.5 cm. Aspect: About 30° from main branch axis. Strength: Strong. Texture and luster: Smooth, glabrous; moderately glossy; becoming woody with development. Color, developing: Close to 143B. Color, developed: Close to 144B; when woody, close to N199A to N199C.

Leaf description:

*Arrangement*.—Opposite, simple.

*Length*.—About 7.2 cm.

*Width*.—About 4.1 cm.

*Shape*.—Broadly elliptic to obovate.

*Apex*.—Apiculate to abruptly acute.

*Base*.—Truncate to obtuse.

*Margin*.—Entire; not lobed.

*Texture and luster, upper and lower surfaces*.—Smooth, glabrous; slightly coriaceous; slightly glossy.

*Venation pattern*.—Pinnate.

*Color*.—Developing leaves, upper surface: Close to 143A. Developing leaves, lower surface: Close to a blend of 146A and 146B. Fully developed leaves, upper surface: Close to NN137A; venation, close to 143B and 143C. Fully developed leaves, lower surface: Close to 146B; venation, close to 145B.

*Petioles*.—Length: About 9 mm. Diameter: About 2 mm by 2 mm. Strength: Moderately strong. Texture and luster, upper surface: Smooth, glabrous; moderately glossy. Texture and luster, lower surface:

Smooth, glabrous; slightly glossy. Color, upper surface: Close to 144B. Color, lower surface: Close to 145A.

Flower description:

*Flower type and flowering habit*.—Single star-shaped salverform flowers arranged in terminal and axillary cymes; flowers face outwardly to slanting upright; freely flowering habit with about five flowers per inflorescence and about 40 flower buds and open flowers developing per plant.

*Natural flowering season*.—Plants flower continuously from spring into the autumn in Germany; plants begin flowering about 10 to 14 weeks after propagation depending on environmental and cultural conditions.

*Flower longevity*.—Individual flowers last about two weeks on the plant; flowers not persistent.

*Fragrance*.—None detected.

*Inflorescence height*.—About 14.1 cm.

*Inflorescence diameter*.—About 11.5 cm.

*Flower buds*.—Length: About 6.2 cm. Diameter: About 1 cm. Shape: Narrowly oblanceolate. Texture and luster: Smooth, glabrous; slightly glossy. Color: Close to a blend of 46A and 53A; proximally, close to 145A and 145B; distally, tinged with close to 53B.

*Flowers*.—Appearance: Flared trumpet, corolla fused and five-parted. Diameter: About 8.5 cm by 8.5 cm. Depth (length): About 6 cm. Throat diameter: About 1.5 cm. Tube length: About 5.4 cm. Tube diameter: Proximally, about 3.5 mm; distally, about 1.7 cm.

*Corolla*.—Quantity and arrangement: Five petals arranged in a single whorl; lower portion of the petals are fused into a funnelform tube. Petal length, tube and free lobes: About 9.1 cm. Petal length, free lobes: About 3.7 cm. Petal width, free lobes: About 3.1 cm. Petal shape and appearance: Unequal and broadly spatulate. Petal apex: Apiculate, unequal. Petal margin: Entire; moderately undulate. Petal texture and luster, upper surface: Smooth, glabrous; velvety; matte. Petal texture and luster, lower surface: Smooth, glabrous; slightly velvety; slightly to moderately glossy. Throat texture: Smooth, glabrous; velvety. Tube texture: Smooth, glabrous; slightly velvety. Color: Petal, when opening, upper surface: Close to N45A; towards the apex, close to 46A. Petal, when opening, lower surface: Close to 53B. Petal, fully opened, upper surface: Close to 53A; venation, close to 53A; color does not fade with subsequent development. Petal, fully opened, lower surface: Close to 185A; venation, close to 46A; with subsequent development, center and towards the base becoming closer to N45A. Throat: Distally, close to 53A; proximally, close to 30A and toward the base, close to 23A and at the base, close to 145B; venation, similar to lamina colors. Tube: Close to a blend of 145D and 150D; distally, tinged with close to 53C; at the base, close to 145B; venation, similar to lamina colors.

*Sepals*.—Quantity and arrangement: Five sepals arranged in a single whorl. Calyx length: About 9 mm. Calyx diameter: About 8 mm. Length: About 9 mm. Width: About 1.75 mm. Shape: Lanceolate. Apex: Narrowly acuminate. Base: Broadly cuneate and fused at the base. Margin: Entire. Texture and luster, upper surface: Smooth, glabrous; slightly glossy. Texture and luster, lower surface: Smooth, glabrous; matte. Color: When developing, upper surface: Close to 145C; at the apex, close to N34D. When developing, lower surface: Close to 144C; at the apex, close to N34D. Fully developed, upper surface: Close to 145B; at the apex, close to N34C. Fully developed, lower surface: Close to 144B; at the apex, close to N34C.

*Peduncles*.—Length: About 7.5 cm. Diameter: About 2.5 mm. Strength: Strong. Aspect: About 25° from lateral branch axis. Texture and luster: Smooth, glabrous; moderately glossy. Color: Close to 143C.

*Pedicels*.—Length: About 1.8 cm. Diameter: About 2.25 mm. Strength: Strong. Aspect: About 35° from peduncle axis. Texture and luster: Smooth, glabrous; slightly glossy. Color: Close to 145A.

*Reproductive organs*.—Stamens: Quantity and arrangement: Typically five; basifixed; anthers connivent. Filament length: About 2 mm. Filament color: Close to 154D. Anther shape: Narrowly oblong. Anther size: About 1.25 mm by 8 mm. Anther color: Close to 158A. Pollen amount: None observed. Pistils: Quantity: Typically one. Pistil length: About 2.1 cm. Style length: About 1.8 cm. Style color: Close to 145C. Stigma diameter: About 2 mm. Stigma shape: Club-shaped. Stigma color: Close to 148D. Ovary color: Close to 144A.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'INMAN 501' as herein illustrated and described.

* * * * *